United States Patent [19]

Liebermann

[11] 4,235,095

[45] * Nov. 25, 1980

[54] DEVICE FOR DETECTING INHOMOGENEITIES SUCH AS GAS BUBBLES

[75] Inventor: Leonard N. Liebermann, La Jolla, Calif.

[73] Assignee: TIF Instruments, Inc., Miami, Fla.

[*] Notice: The portion of the term of this patent subsequent to Feb. 13, 1996, has been disclaimed.

[21] Appl. No.: 939,058

[22] Filed: Sep. 1, 1978

Related U.S. Application Data

[63] Continuation-in-part of Ser. No. 826,689, Aug. 22, 1977, Pat. No. 4,138,879.

[51] Int. Cl.³ .............................................. G01N 29/02
[52] U.S. Cl. ........................................ 73/19; 73/61 R; 62/127
[58] Field of Search ............... 73/19, 61; 62/127, 149

[56] References Cited

U.S. PATENT DOCUMENTS

| 2,573,390 | 10/1951 | Blanchard | 73/19 |
| 3,974,681 | 8/1976 | Namery | 73/19 |
| 4,138,879 | 2/1979 | Liebermann | 73/19 |

Primary Examiner—Herbert Goldstein
Attorney, Agent, or Firm—Pennie & Edmonds

[57] ABSTRACT

A detector comprises a pair of electromechanical transducers for disposition on a fluid-filled conduit in an acoustically coupled relationship, an adjustable gain driving amplifier responsive to the electrical output of one transducer for driving the other transducer, an automatic gain control circuit for automatically adjusting the gain of the driving amplifier maintaining the system on the margin of oscillation, and an indicating circuit for detecting modulation of the driving signal. Bubbles passing through the conduit increase the gain required to maintain the system on the margin of oscillation, and are detected as modulations of the driving signal. In a preferred embodiment, this bubble detector is utilized as a refrigerating system test instrument.

5 Claims, 5 Drawing Figures

DEVICE FOR DETECTING INHOMOGENEITIES SUCH AS GAS BUBBLES

CROSS-REFERENCE TO RELATED APPLICATIONS

This application is a continuation-in-part of application Ser. No. 826,689, filed Aug. 22, 1977, now U.S. Pat. No. 4,138,879.

BACKGROUND OF THE INVENTION

This invention relates to a device for detecting inhomogeneities such as gas bubbles in a fluid in a conduit such as a liquid and, more particularly, to a device for detecting bubbles in liquid-filled pipes.

The detection of inhomogeneities such as bubbles within a fluid, for example a liquid, is of importance in monitoring and controlling a wide variety of processes. In high temperature processes using liquid coolants, for example, the presence of inhomogeneities in the form of bubbles can indicate regions of heat transfer deterioration. As another example, in refrigeration systems the presence of bubbles provides an indication of refrigerant insufficiency.

The usual technique for detecting bubbles within a pipe or conduit, however, is visual observation through a sight glass or other window. This technique requires a human observer and is not readily automated. Moreover, it cannot be used in much existing equipment, such as many automotive and home air conditioners which have no sight glasses or viewing windows.

In the instance of automotive and home air conditioners, the unavailability of sightless bubble detectors has contributed to a definite environmental problem. Upon suspicion of refrigerant insufficiency, it is common practice to empty all of the refrigerant gas, usually freon, into the atmosphere and to refill the system with the factory specified amount. The discharge of such gases into the atmosphere has a now well-recognized detrimental effect on the earth's protective ozone layer. See the Report of the Federal Task Force on Inadvertent Modification of the Stratosphere, *Fluorocarbons and the Environment* (U.S. Gov.'t., 1975).

While devices exist for automatically monitoring the bubble content of relatively large samples of open water, these devices are inappropriate for the non-obstructive monitoring of liquids contained in small diameter pipe or conduit. U.S. Pat. No. 3,046,780, for example, issued to the present inventor on July 31, 1962, discloses a fluid condition monitor comprising a towable acoustic resonator and a pair of coupled transducers. Impurities or disturbances in the fluid through which the device is towed are detected by variations in the quality factor, Q, of the resonating system. While it is suggested that this device can be used in pipelines, it would clearly be preferable to utilize a detection device which need not be placed within the pipe or conduit and thereby obstruct or impede fluid flow. Moreover, many pipes and conduits of interest have a sufficiently small diameter that impractically small resonators and impractically high frequency transducers would be required.

SUMMARY OF THE INVENTION

In accordance with the present invention, a detector comprises a pair of electromechanical transducers for disposition on a fluid-filled conduit in an acoustically coupled relationship, an adjustable gain driving amplifier responsive to the electrical output of one transducer for driving the other transducer, an automatic gain control circuit for automatically adjusting the gain of the driving amplifier maintaining the system on the margin of oscillation, and an indicating circuit for detecting modulation of the driving signal. Inhomogeneities such as bubbles passing through the conduit near the transducers cause variations, for example an increase, in the gain required to maintain the system on the margin of oscillation, and are detected as modulations of the driving signal. In a preferred embodiment, this detector is utilized as a refrigeration test instrument. The advantages of this detector are (1) it does not require a sight glass or window for visual observation; (2) it does not obstruct the flow of fluid; (3) it does not require penetration of the conduit; and (4) it can be readily incorporated into automatic monitoring systems.

BRIEF DESCRIPTION OF THE DRAWINGS

The nature, advantages, and various features of the invention will appear more fully upon consideration of the illustrative embodiments now to be described in detail in connection with the accompanying drawings.

In the drawings.

For convenience of reference, similar elements are denoted by the same reference numeral throughout the drawings.

DETAILED DESCRIPTION OF THE DRAWINGS

Figure 1:
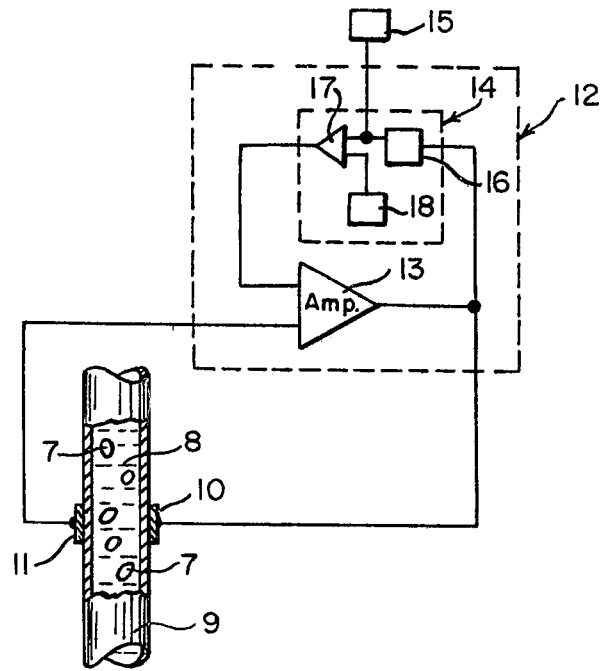
FIG. 1 is a schematic block diagram of a bubble detection device in accordance with the invention.

Referring to the drawings, FIG. 1 schematically illustrates a detector in accordance with the invention for detecting gas bubbles or other inhomogeneities 7 in a liquid or other fluid 8 within pipe or conduit 9. In substance, the detector comprises a pair of electromechanical transducers 10 and 11, a feedback driving circuit with automatic gain control 12 comprising driving amplifier 13, such as an operational amplifier, and automatic gain control circuit 14, and an indicating circuit 15.

Transducers 10 and 11 are preferably barium titanate crystals cut and mounted to respectively transmit and receive compression vibrations. Preferably, they are coupled to the pipe by rubber mountings (not shown) for rejecting shear oscillations.

Automatic gain control circuit 14 (AGC circuit) is a circuit arrangement well-known in the art for preventing swings in the output of an amplifier, such as driving amplifier 13, beyond a predefined excursion range. It consists essentially of a feedback conditioning circuit 16, such as a half-wave detector, for defining the feature of the output of driving amplifier 13 to be constrained, a feedback amplifier 17, and a sensitivity control 18.

In the preferred operation of the device of FIG. 1, acoustic waves from transmitting transducer 10 pass through conduit 9, liquid 8, and any bubbles passing between or near the two transducers to receiving transducer 11. Receiving transducer 11 converts the received acoustic waves into electrical signals which in turn are applied to the input of AGC controlled driving amplifier 13.

The AGC circuit 14, responsive to the output of amplifier 13, is adjusted to maintain the system comprising the transducers and the driving amplifier at a predetermined operating point. Preferably, for maximum sensitivity, the AGC circuit is adjusted to maintain the system on the margin of oscillation. Should inhomogeneities such as bubbles pass between or near transducers 10 and 11, the acoustic signal reaching transducer 11 will be altered by the different acoustic properties of the inhomogeneity, for example, the signal will be attenuated by the higher acoustic absorption of a gas in a liquid resulting in an attenuated electrical input to amplifier 13. AGC circuit 14 alters the gain of amplifier 13, as necessary, to produce a change in the driving signal that will quickly restore the system to its operating point on the margin of oscillation. The resulting changes in the driving signal can be conveniently metered by indicator 15 monitoring the output of amplifier 13.

Figure 2:
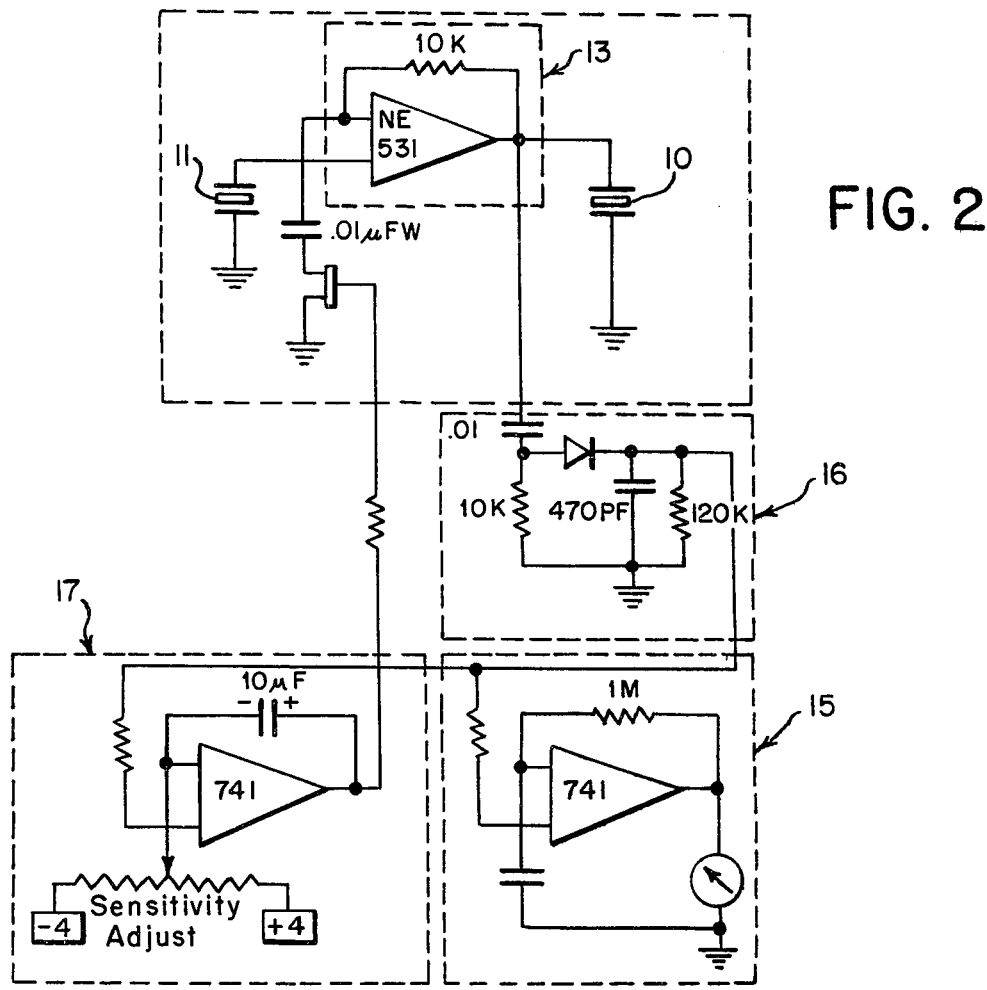
FIG. 2 is a circuit diagram of a preferred automatic refrigeration test instrument employing the bubble detection device of FIG. 1.

FIG. 2 shows a detailed circuit diagram of a preferred feedback driving circuit for this device. Here the output of driving amplifier 13 is applied to half-wave detector 16 for conditioning in accordance with its average half-wave value. Indicator circuit 15 is a conventional circuit for receiving this average half-wave value from the output of circuit 16, amplifying it for display and displaying it on a voltmeter. Feedback amplifier 17 is a simple differential amplifier with a potentiometer sensitivity adjustment. The components in this circuit are all standard items and have the manufacturer's type numbers and values of resistance and capacitance set forth in the drawing. This circuit is designed to operated at a frequency of about 200 kilohertz.

As can be readily appreciated, this detector does not require a sight glass or a window for visual observation of the liquid or other fluid within the conduit. It does not obstruct the flow of fluid in the conduit, nor does it require penetration of the conduit. Furthermore, since inhomogeneities are detected as variations in an electrical signal, the detector can be readily incorporated into automatic monitoring systems.

Figure 2A:
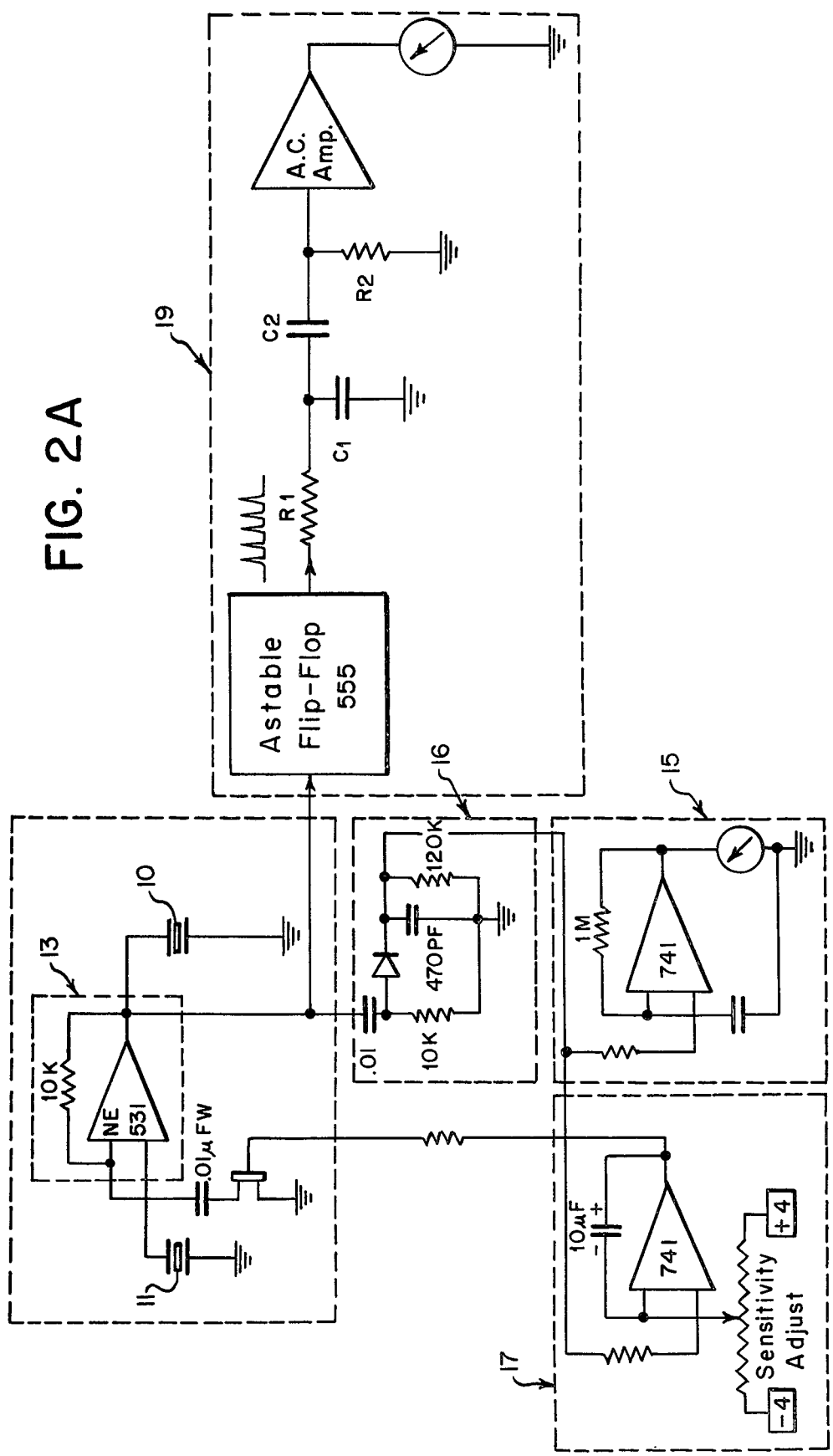
FIG. 2A is a circuit diagram of another preferred automatic refrigeration test instrument employing the bubble detection device of FIG. 1.

FIG. 2A shows a detailed diagram of another preferred feedback driving circuit for this device. In this alternate embodiment, the output of the driving amplifier 13 is applied, in addition to half-wave detector 16, simultaneously to an FM detection circuit 19. The FM detection circuit 19 includes an astable flip-flop or multivibrator which produces pulses of constant height and width and of identical frequency as the sine wave output of the driving amplifier 13. These pulses are smoothed by a series resistor $R_1$ to place a DC potential across capacitor $C_1$. The magnitude of the DC potential is proportional to the frequency of the smoothed signal. Thus, a variation in the frequency or a phase change results in an AC potential applied to the input of an AC amplifier through a second capacitor $C_2$ whose capacitance is much greater than the capacitance of capacitor $C_1$. The circuit comprising $R_1$, $C_1$, $R_2$ and $C_2$ is a filter which smooths and passes frequency variations of said driving signal to the input of the AC Amplifier due to inhomogeneities passing between or near the transducers 10 and 11. For the operational frequency of the preferred embodiment described above in connection with the description of FIG. 2, the RC constant of the $R_1C_1$ circuit is approximately $5 \times 10^{-5}$ sec. while the RC constant of the $R_2C_2$ circuit is approximately one order of magnitude larger, or approximately $5 \times 10^{-4}$ sec. The output of the AC Amplifier reflects changes in the driving signal and may be conveniently displayed, for example on a meter. The FM detection circuit may be utilized either in lieu of the amplitude monitoring discussed with respect to the embodiment illustrated in FIG. 2 or as an add on so that both amplitude and frequency changes may be monitorized.

Figure 3:
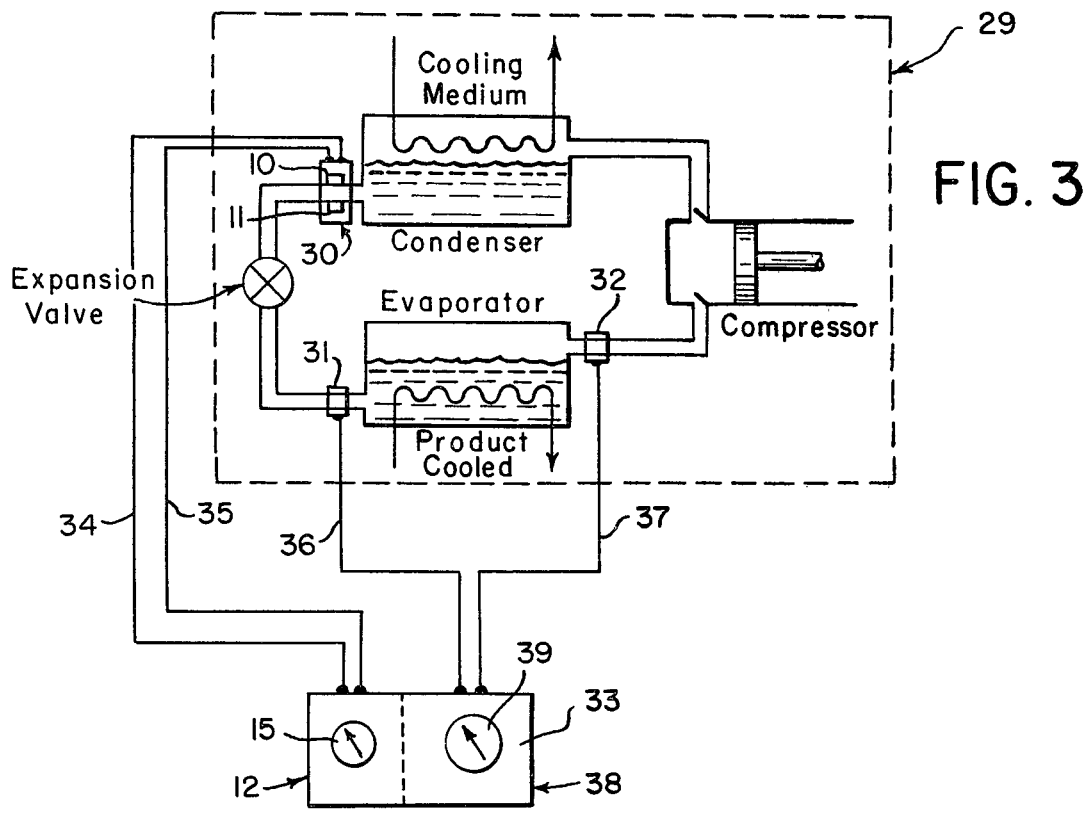
FIG. 3 is a circuit diagram of a preferred automatic refrigeration test instrument employing the bubble detection

FIG. 3 schematically illustrates a refrigeration test instrument, in accordance with a further embodiment of the invention, for diagnosing the state of a refrigerating system 29. Specifically, the test instrument comprises a bubble detector of the type shown in FIGS. 1 and 2 with transducers 10 and 11 preferably mounted in clamp 30 for disposition on the refrigerant tube and a pair of contact temperature sensor 31 and 32 for disposition in contact with the refrigerant tube on either side of the evaporator. Conveniently, the transducers and the temperature sensors are electrically connected to a circuit box 33 by flexible wires 34, 35, 36 and 37, respectively.

In a preferred embodiment, temperature sensors 31 and 32 are silicon diodes whose voltage drop, as is well-known, is a linear function of temperature. A temperature differential indicating circuit 38 is conveniently provided in box 33 for determining the difference between the sensed temperature and displaying on a meter 39.

Figure 4:
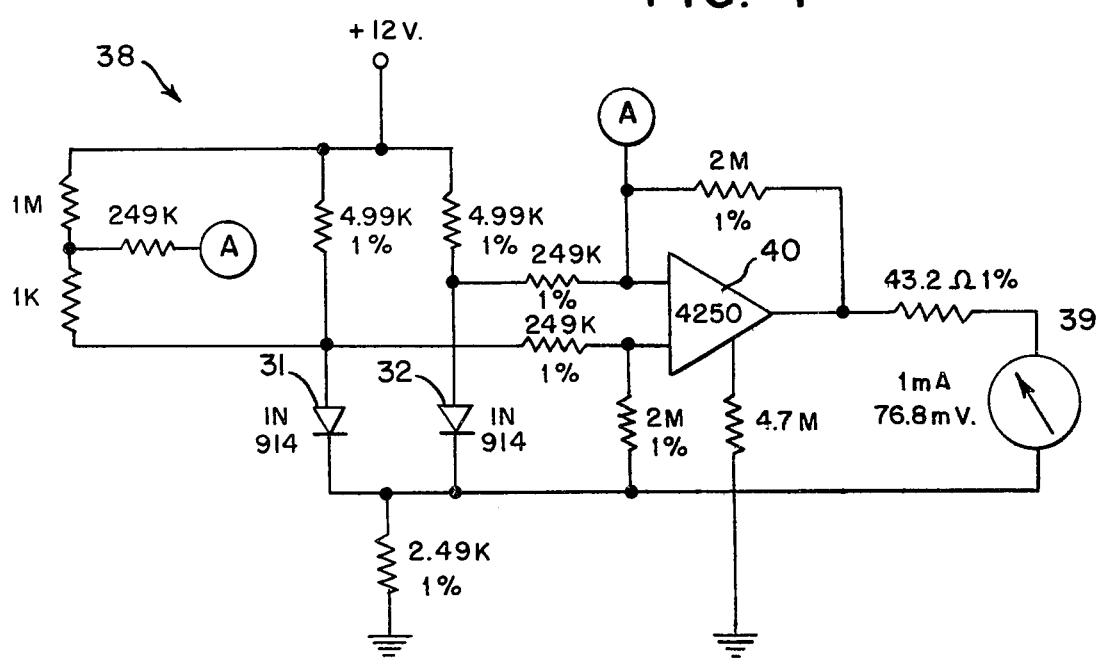
FIG. 4 is a circuit diagram of a preferred temperature sensing circuit useful in the embodiment of FIG. 3.

FIG. 4 illustrates a preferred temperature differential indicating circuit 38. Diodes 31 and 32 are disposed in thermal contact with the refrigerant tube at the input and output of the evaporator, respectively. A voltage is applied across the diodes, and circuit means in the form of differential amplifier 40 and meter 39 is provided for detecting, amplifying, and displaying the temperature-induced difference in voltage drops across the diodes 31 and 32. The components of this circuit are all standard items and have the manufacturer's type numbers and values of resistance and capacitance set forth in the drawing.

In operation, the temperature sensors are disposed on the refrigerant input conduit to the evaporator and the output conduit. If the evaporator is filled with refrigerant, the temperature difference between the input and the output will be zero or negative, i.e., the output being lower in temperature than the input. If the temperature difference is positive, the amount of refrigerant may be inadequate but is not necessarily so. This ambiguity is resolved by applying the bubble detector to the refrigerant conduit in one of three places: near the condenser output, near the expansion valve, or, in capillary systems, near the capillary tube. If bubbles are detected, the system requires additional refrigerant. If no bubbles are detected, they must be made to occur, as by inhibiting cooling air to the condenser, and the temperature difference should be tested again under these new conditions. The refrigerant charge is adequate under these conditions only if the temperature differential is zero or negative.

An alternate preferred embodiment for diagnosing the state of a capillary or orifice type refrigerating system contemplates a variation of the refrigerating system 29 in which there is no need for the temperature sensors.

In this embodiment (not shown), the test instrument comprises an inhomogeneity detector of the type shown in FIGS. 1 and 2 or 2A with transducers 10 and 11 preferably mounted in clamp 30 for disposition on the refrigerant output conduit, the low pressure side of the evaporator, generally near the evaporator.

In operation a quantity of refrigerant will periodically splash into the refrigerant output conduit so long as there is a sufficient quality of refrigerant in the system. The liquid refrigerant entering the output conduit which is predominatly vapor-filled will be detected as an inhomogeneity moving past the transducer, to thereby cause a change in the driving signal of the detector. As long as the splashing persists, inhomogeneities will be detected indicating an adequate quantity of refrigerant in the system. Conversely, after the splashing ceases, a situation that will occur if the quanitity of the refrigerant becomes inadequate, there will be no inhomogeneities in the refrigerant output conduit, and therefore no changes in the driving signal will be detected, which will indicate that the amount of refrigerant in the system is inadequate.

While the invention has been described in connection with only a small number of specific embodiments, it is to be understood that these are merely illustrative of the many other specific embodiments which can also utilize the principles of the invention. Numerous and varied devices can be made by those skilled in the art without departing from the spirit and scope of the present invention, as defined by the following claims.

I claim:

1. A device for detecting inhomogeneities in a fluid within a conduit comprising: a pair of electromechanical transducers for disposition on such conduit in an acoustically coupled relationship; adjustable gain driving amplifier means responsive to the electrical output of one of said transducers for providing a driving signal for driving the other of said transducers; automatic gain control circuit means connected to the output and at least one input of said driving amplifier means for automatically adjusting the gain of said driving amplifier to maintain said transducers and said amplifier at a predetermined operating point; and indicating circuit means connected to said amplifier for indicating changes in at least one of amplitude and frequency of said driving signal caused by an inhomogeneity in said fluid moving past said transducers.

2. A device according to claim 1 wherein said indicating circuit means comprises means for detecting changes in frequency.

3. A device according to claim 2 wherein said FM detection means comprises means for producing pulses of uniform height and means for producing an AC potential in response to variations in frequency of the signal being detected.

4. A method of detecting inhomogeneities in a fluid within a conduit comprising: transmitting acoustical vibrations by a first transducer disposed on one side of the conduit; receiving the transmitted vibrations by a second transducer disposed on the opposite side of the conduit; converting the received vibrations into electrical signals; amplifying the electrical signals by an adjustable gain driving amplifier means for providing a driving signal for driving the first transducer; automatically adjusting the gain of said driving amplifier for maintaining said transducers and said amplifier means at a predetermined operating point; and indicating changes in at least one of amplitude and frequency of the driving signal caused by an inhomogeneity in the fluid moving past said transducers.

5. A method of testing a refrigerating system of the capillary type utilizing a refrigerant, a refrigerant tube and an evaporator comprising: transmitting acoustical vibrations by a first electromechanical transducer disposed on the low pressure side of the evaporator on one side of the refrigerant tube, receiving the transmitted vibrations by a second electromechanical transducer disposed on the low pressure side of the evaporator on the refrigerant tube in an acoustically coupled relationship with said first transducer; converting the received vibrations into electrical signals; amplifying the electrical signals by an adjustable gain driving amplifier means for providing a driving signal for driving said first transducer; automatically adjusting the gain of said driving amplifier for maintaining said transducers and said amplifier means at a predetermined operating point; periodically splashing refrigerant into the refrigerant tube so long as a predetermined minimum quantity of said refrigerant is present in the refrigerating system so that a detectable quantity of said refrigerant moves past said transducers; and indicating changes in at least one of amplitude and frequency of the driving signal caused by said refrigerant in the refrigerant tube moving past said transducers, whereby said detected changes in the driving signal indicates an adequate quantity of refrigerant in the refrigerating system.

* * * * *